(12) United States Patent
Czajka et al.

(10) Patent No.: US 7,343,919 B2
(45) Date of Patent: Mar. 18, 2008

(54) SURGICAL DRAPE WITH A POUCH

(75) Inventors: Francis A. Czajka, Libertyville, IL (US); Kristi R. Camasta, Antioch, IL (US)

(73) Assignee: Medline Industries, Inc., Mundelein, IL (US)

(*) Notice: Subject to any disclaimer, the term of this patent is extended or adjusted under 35 U.S.C. 154(b) by 0 days.

(21) Appl. No.: 11/397,159

(22) Filed: Apr. 4, 2006

(65) Prior Publication Data

US 2006/0219249 A1 Oct. 5, 2006

Related U.S. Application Data

(60) Provisional application No. 60/667,967, filed on Apr. 4, 2005.

(51) Int. Cl.
*A61B 19/00* (2006.01)
*A61B 19/08* (2006.01)
*A61F 5/37* (2006.01)

(52) U.S. Cl. .................. 128/849; 128/850; 128/852; 128/853

(58) Field of Classification Search ......... 128/849–856
See application file for complete search history.

(56) References Cited

U.S. PATENT DOCUMENTS

| | | | | |
|---|---|---|---|---|
| 3,882,859 A * | 5/1975 | Ericson | ............ | 128/854 |
| 4,051,845 A | 10/1977 | Collins | ............ | 128/132 |
| 4,169,472 A | 10/1979 | Morris | ............ | 128/132 |
| 4,316,455 A * | 2/1982 | Stoneback | ............ | 128/853 |
| 4,323,062 A | 4/1982 | Canty | ............ | 128/132 |
| 4,489,720 A | 12/1984 | Morris et al. | ............ | 128/132 |
| RE31,887 E * | 5/1985 | Hodgson | ............ | 428/40 |
| 4,559,937 A | 12/1985 | Vinson | ............ | 128/132 |
| 4,570,628 A | 2/1986 | Neal | ............ | 128/132 |
| 4,598,458 A | 7/1986 | McAllester | ............ | 128/132 |
| 4,616,642 A | 10/1986 | Martin et al. | ............ | 128/132 |
| 4,745,915 A | 5/1988 | Enright et al. | ............ | 128/132 |
| 4,807,644 A | 2/1989 | Sandhaus | ............ | 128/849 |
| 4,867,177 A | 9/1989 | Urheim | ............ | 128/849 |
| 4,869,271 A | 9/1989 | Idris | ............ | 128/853 |
| 4,890,628 A | 1/1990 | Jackson | ............ | 128/849 |
| 4,957,120 A | 9/1990 | Grier-Idris | ............ | 128/849 |
| 4,974,604 A | 12/1990 | Morris | ............ | 128/853 |
| 5,002,069 A * | 3/1991 | Thompson et al. | ............ | 128/849 |
| 5,036,866 A | 8/1991 | Eldrige, Jr. et al. | ............ | 128/849 |
| 5,074,316 A | 12/1991 | Dowdy | ............ | 128/849 |
| 5,143,091 A * | 9/1992 | Patnode et al. | ............ | 128/853 |
| 5,209,243 A | 5/1993 | Glassman | ............ | 128/849 |
| 5,287,860 A | 2/1994 | Owens | ............ | 128/851 |
| 5,322,071 A | 6/1994 | Ambrose | ............ | 128/849 |
| 5,339,831 A | 8/1994 | Thompson | ............ | 128/852 |
| 5,419,343 A | 5/1995 | Taylor | ............ | 128/849 |
| 5,494,050 A | 2/1996 | Reyes | ............ | 128/849 |
| 5,599,617 A * | 2/1997 | Ewald | ............ | 428/317.3 |
| 5,618,278 A | 4/1997 | Rothrum | ............ | 604/356 |

(Continued)

*Primary Examiner*—Justine R. Yu
*Assistant Examiner*—Kristen C. Matter
(74) *Attorney, Agent, or Firm*—Nixon Peabody LLP

(57) ABSTRACT

A surgical drape having a sheet. The sheet includes a distal side and a proximal side relative to a surgical patient. The drape also includes a surgical pouch connected to the distal side of the sheet. The surgical pouch is connected to the sheet via at least two elastomeric portions.

25 Claims, 2 Drawing Sheets

U.S. PATENT DOCUMENTS

| | | | |
|---|---|---|---|
| 5,640,975 A | 6/1997 | Diao | 128/853 |
| 5,647,376 A | 7/1997 | Thompson | 128/853 |
| 5,765,566 A * | 6/1998 | Rothrum | 128/849 |
| 5,871,014 A | 2/1999 | Clay et al. | 128/849 |
| 5,960,794 A | 10/1999 | Shaw | 128/849 |
| 6,032,670 A * | 3/2000 | Miller | 128/849 |
| 6,070,586 A | 6/2000 | Harroll et al. | 128/849 |
| 6,105,578 A | 8/2000 | Sommers et al. | 128/849 |
| 6,129,085 A | 10/2000 | Jascomb | 128/849 |
| 6,179,819 B1 | 1/2001 | Haswell | 604/356 |
| 6,199,553 B1 | 3/2001 | Hafer et al. | 128/849 |
| 6,213,124 B1 | 4/2001 | Butterworth | 128/853 |
| 6,269,815 B1 | 8/2001 | Jascomb | 128/849 |
| 6,314,958 B1 | 11/2001 | Harroll et al. | 128/849 |
| 6,725,864 B2 | 4/2004 | Ewonce et al. | 128/849 |
| 6,820,622 B1 | 11/2004 | Teves et al. | 128/849 |
| 2002/0174870 A1 | 11/2002 | Ewonce et al. | 128/853 |
| 2003/0188753 A1 | 10/2003 | Jascomb | 128/853 |
| 2004/0045557 A1 | 3/2004 | Lee et al. | 128/853 |
| 2004/0190139 A1 | 9/2004 | Weaver et al. | 359/510 |
| 2005/0061330 A1* | 3/2005 | Fenwick et al. | 128/849 |
| 2005/0066977 A1* | 3/2005 | Gavette et al. | 128/849 |
| 2006/0150987 A1* | 7/2006 | Dillion et al. | 128/849 |

* cited by examiner

SURGICAL DRAPE WITH A POUCH

CROSS-REFERENCE TO RELATED APPLICATION

This application claims the benefit of U.S. Provisional Application No. 60/667,967, filed Apr. 4, 2005, which is hereby incorporated by reference in its entirety.

FIELD OF THE INVENTION

This invention relates to surgical drapes, and more specifically to surgical drapes used in surgeries, the drape having pouches with elastomeric corners and/or anti-slip patient positioners.

BACKGROUND OF THE INVENTION

This invention relates to surgical drapes for use in surgical procedures. The drape is of particular value in arthroscopic and open procedures in which significant amounts of bodily fluids are released and/or irrigation of the surgical site is used. The fluids are collected in a pouch associated with the drape and removed for disposal. The pouches may also be used for supporting the dead weight of a limb during surgery, such as in hip surgery, or for holding instruments during the surgery. In other uses, pouches may also be used to collect fluid during the surgery.

While there are surgical drapes having pouches available on the market, they are not always as satisfactory as would be desired. During some types of surgery, the pouch is used to support the dead weight of a limb or to hold an instrument. However, because of the design of the available pouches, they are subject to tearing if the weight is too great. In surgeries in which the pouch is supporting a limb, this can cause the limb to move during surgery. In surgeries in which the pouch is used to hold an instrument, the tearing of the pouch can cause the instrument to fall to the ground, contaminating the instrument.

Another problem with current surgical drapes is that the drape may slip during surgery, causing the surgical site to become obstructed or causing the contamination of the surgical site and/or sterile instruments.

To meet the need for an improved surgical drape for use in surgical procedures, the present inventors have developed the drape with a pouch shown in the drawings and described below.

SUMMARY OF THE INVENTION

According to one embodiment of the present invention, a surgical drape is provided. The surgical drape has a sheet with a distal side and a proximal side (relative to a surgical patient). A pouch is also included and is connected to the distal side of the sheet and includes at least two elastomeric portions, which allow the pouch to stretch away from the sheet.

According to another embodiment of the present invention, a method of making a surgical drape is provided. The method includes providing a sheet and a pouch. The sheet has a distal side and a proximal side relative to a surgical patient. The pouch includes one or more elastomeric portions, which allow the pouch to stretch away from the sheet.

According to yet another embodiment of the present invention, a surgical drape is provided having a distal side and a proximal side relative to a surgical patient. The proximal side of the drape includes a fastener for attaching the drape to a surface. Also included is at least one anti-slip patient positioner attached to the proximal side.

According to yet another alternative embodiment, a method of making a surgical drape is provided. The method includes providing a drape, the drape having a distal side and a proximal side relative to a surgical patient's body. Attached to the surgical drape is a fastener that is used to attach the drape to a surface. An anti-slip patient positioner is also attached to the proximal side of the drape.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

Figure 1:
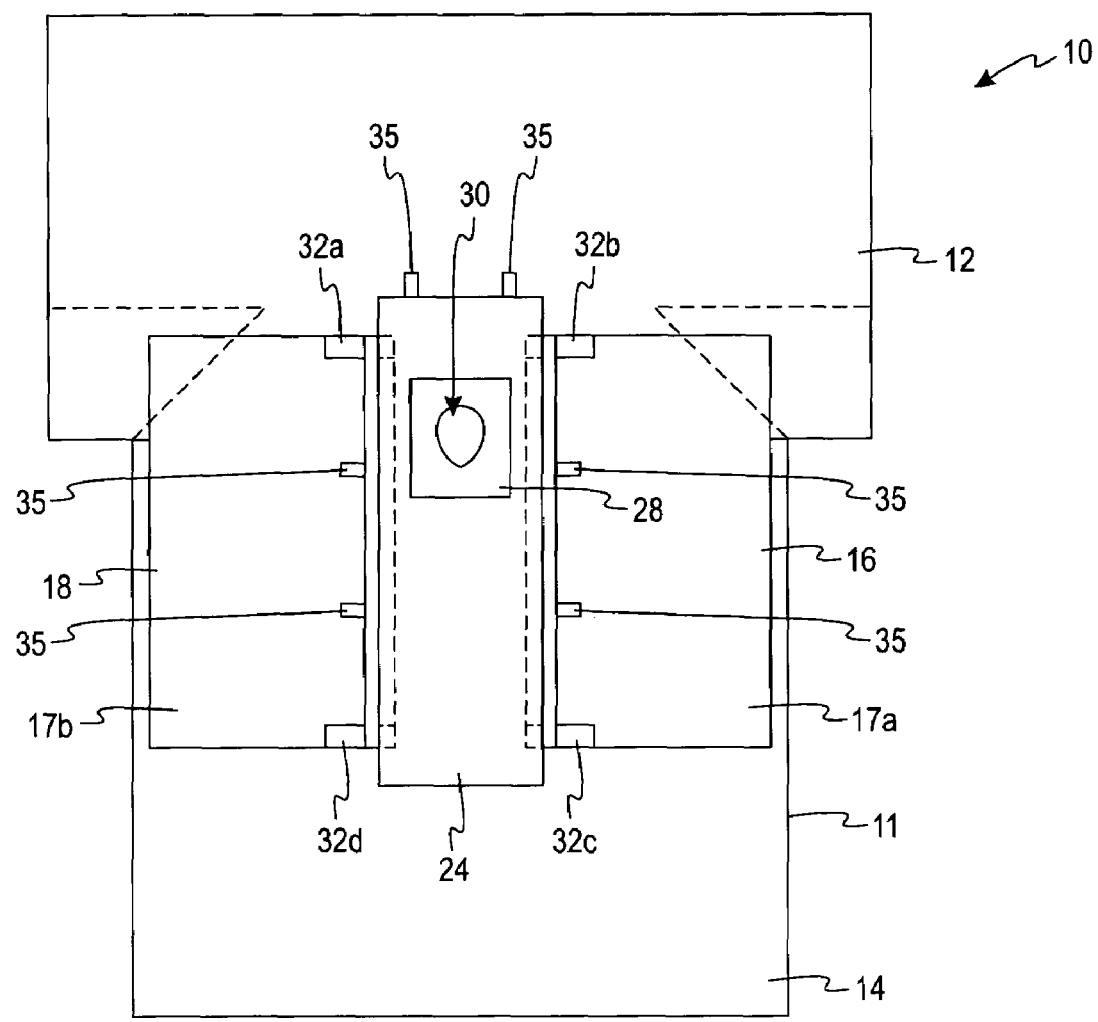
FIG. 1 is a plan view of the distal side of a surgical drape of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF THE PREFERRED EMBODIMENTS

FIG. 1 shows the distal side of a surgical drape 10 according to one embodiment as it would appear after being unfolded and ready for use in surgery. In this embodiment, the surgical drape 10 is to be used in hip surgery. However, the inventive drape could be used on any drape that could be used in any type of surgery, including, but not limited to, open, laparoscopic, endoscopic, and arthroscopic surgery. The surgical drape 10 may be made of any standard medical fabric, including non-woven and woven fabrics, such as, but not limited to spunlace, spunbond meltblown spunbond (SMS), bi-component non-woven materials, tri-laminates, bi-laminates, combinations thereof, and/or any variation of such fabrics. Such materials may be manufactured by DuPont of Old Hickory, Tenn., BBA of Simpsonville, S.C., Fiberweb of Simpsonville, S.C., First Quality Non-Wovens of Great Neck, N.Y., Ahlstrom of Windsor Locks, Conn., Arjo Wiggins of Columbia, S.C. and PGI of Mooresville, N.C. to name a few.

Figure 2:
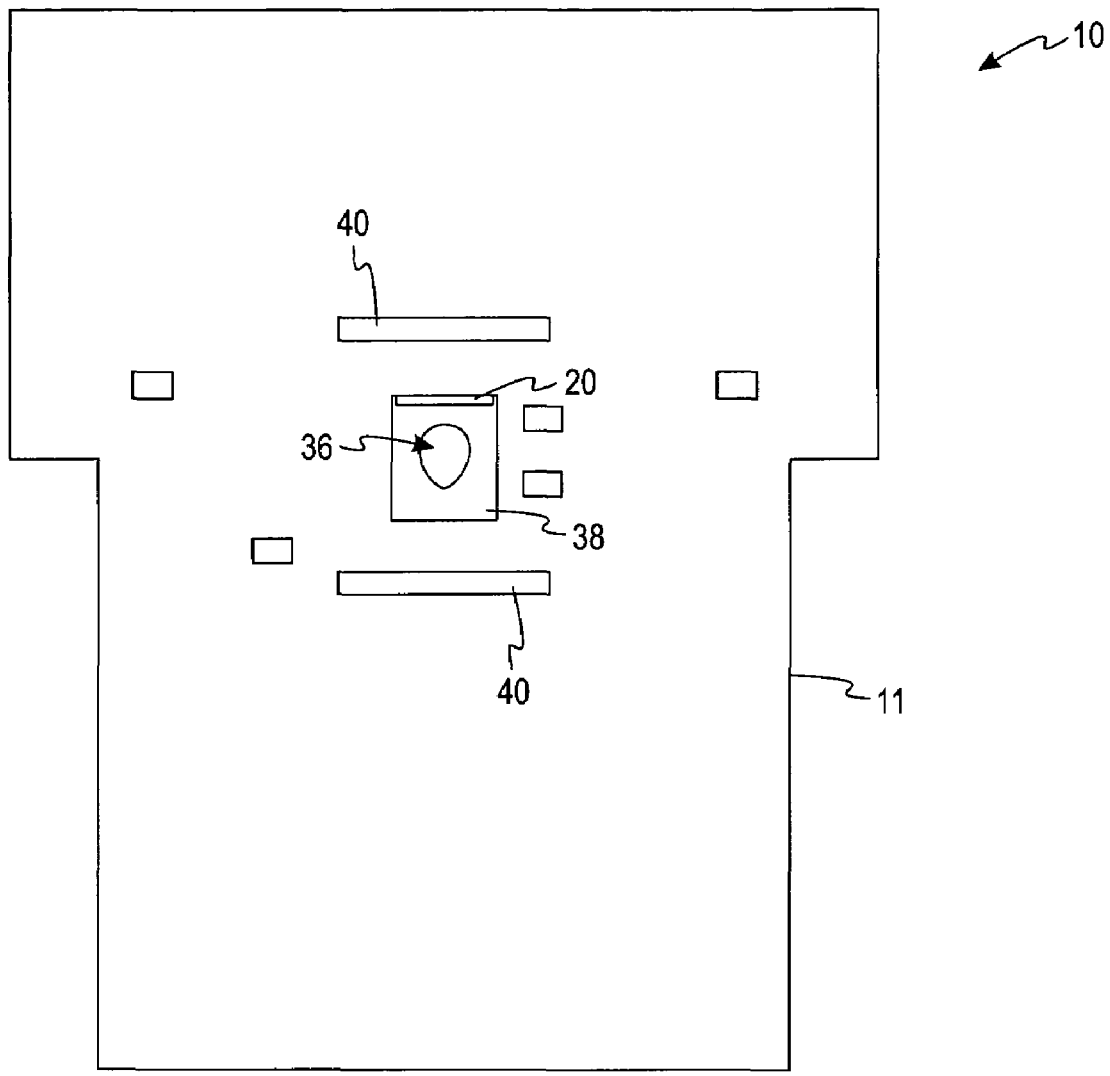
FIG. 2 is a plan view of the reverse (proximal) side of the surgical drape of FIG. 1.

The proximal side (i.e., the patient's side) is shown in FIG. 2. In one embodiment, the drape 10 includes a sheet 11 that is generally T-shaped, having a top portion 12 and a bottom portion 14. The top portion 12 has a width from about 100 inches to about 120 inches and a length from about 50 inches to about 70 inches in one embodiment. The bottom portion 14 has a width from about 80 inches to about 100 inches and a length from about 50 inches to about 70 inches in one embodiment. In one embodiment, the top portion 12 has a width of about 112 inches and a length of about 58 inches and the bottom portion 14 has a width of about 89 inches and a length of about 59 inches. Any of the dimensions may be varied depending on the patient's size, the type of surgery, or other practical considerations. Many other dimensions may be used. Also, the drape 10 need not be in a T-shape or in a general T-shape; it may be square, generally square, rectangular, generally rectangular, oblong, generally oblong, or any other shape useful for providing a drape during surgery.

In the center of the drape 10 are longitudinal panels 16 and 18, which form pouches 17a, 17b. The longitudinal panels 16 and 18 may be made of a plastic material or any standard medical fabric, including non-woven and woven fabrics, such as, but not limited to spunlace, spunbond meltblown spunbond (SMS), bi-component non-woven materials, tri-laminates, bi-laminates, combinations thereof, and/or any variation of such fabrics. The longitudinal panels 16 and 18 may be made of a clear or partially clear plastic material, a polyethylene, or a non-woven material. In some embodiments, only one panel may be used. In other embodiments, more than two longitudinal panels may be used.

In other embodiments, the pouches 17a, 17b may be placed elsewhere on the drape, depending on the purpose of the pouch (e.g., to collect fluids, hold instruments, support limbs, etc.). Although generally rectangular pouches 17a, 17b are shown, other shapes, such as squares, circles, etc. may be used. The dimensions of the pouches 17a, 17b may vary. The longitudinal panels 16, 18 may be outlined by a wire (not shown) around the upper edges. When the drape 10 is in position, the wire-outlined edge tends to fall outward to naturally open the pouches 17a, 17b to receive fluids during surgery. Depending on the use for the pouches 17a, 17b, the pouches 17a, 17b may be troughs, meaning that the pouches are open on the top and sides, or the pouches 17a, 17b may be pockets, meaning that the pouches are only open on one side.

Tape 20 (FIG. 2) is located on one edge of a elastomeric portion 38, which is described later, and is used to attach the drape 10 to either the patient's body or another stationary surface, such as the operating table or another drape. In one embodiment, the tape 20 may be between about 1 inch to about 2 inches wide. The tape 20 may be of type manufactured for surgical drape applications, such as by the 3M Company of St. Paul, Minn. or Avery Dennison of Pasadena, Calif. The tape dimensions may vary from these values. The tape dimensions may be varied depending on the actual size of the drape. Other fastening devices such as, but not limited to, adhesives, glue, buttons, snaps, hook and loop fasteners, such as VELCRO®, and/or any other type of surgical tape or glue may also be used to attach the drape 10 to a stationary surface or to a patient's body.

The drape 10 also includes at least one reinforcement 24. The reinforcement 24 surrounds the surgical site and, in this embodiment, accepts, absorbs, or repels fluids released during surgery for disposal. Alternatively, or in addition to accepting, absorbing, or repelling fluids, the reinforcement 24 may be used for holding instruments and/or supporting the dead weight of a limb(s) during surgery. The reinforcement 24 may be attached to the drape 10 via a fastening device such as, but not limited to, adhesives, glue, buttons, snaps, hook and loop fasteners, such as VELCRO®, and/or any other type of surgical tape or glue.

In one embodiment, the reinforcement 24 is made of a generally fluid impervious material, such as foam, non-woven, or laminate materials. In the embodiment illustrated in FIG. 1, the reinforcement 24 extends from slightly above the longitudinal panels 16 and 18 to slightly below the longitudinal panels 16 and 18 and is shaped so as to direct the flow of fluids into the pouches 17a, 17b for disposal. The exact location and size of the reinforcement 24 may vary than that shown.

In some embodiments, particularly those in which the reinforcement 24 is used to hold a limb, the reinforcement 24 also includes a panel 28 with a fenestration 30 to help avoid tearing of the fenestration 30 during use. The panel 28 may be elastomeric or non-elastomeric. The panel 28 may be attached to the drape 10 via an adhesive glue or surgical tape. Other types of fasteners may also be used such as other types of tape, snaps, buttons, hook and loop fastener, such as VELCRO®, and/or other suitable fasteners. In one embodiment, the panel 28 has a width from about 7 inches to about 15 inches and a length of about 7 inches to about 15 inches. The dimensions of the elastomeric panel 28 may vary from these values. The dimensions may be varied depending upon the limb to be held (whether an arm or leg), the type of surgery, the dimensions of the drape, and the like. Although a generally square, elastomeric, panel 28 is shown, other shapes, such as rectangles, circles, etc. may be used.

The fenestration 30 is adapted to accept the patient's leg (or other body part, such as an arm) to facilitate surgery. The fenestration 30 is, in one embodiment, approximately a nine inch pear-shaped fenestration. These dimensions and shapes may vary. The dimensions and shapes of the fenestration 30 may vary based upon the size of the limb to be held, the size of the elastomeric panel, the position of the drape 10 on the body (e.g., where on the body the drape 10 will be covering), etc . . . In some embodiments, the flexibility of the panel 28 allows the fenestration 30 to conform to the patient's leg or other body part so as to prevent surgical and/or bodily fluids from leaking during the surgery and to create isolation during the surgery. The panel 28 may be formed from any suitable material such as KRATON™, which is manufactured by Clopay Company of Augusta, Ky., or any other elastomeric, elastic, and/or stretchable materials. The panel 28 may also be formed of any other material which allows the fenestration 30 to expand to hold a limb. It is also contemplated that any other material for achieving the goal of having a fenestration may be used. In some embodiments, the fenestration 30 may not be elastomeric, but instead may be a cut-out.

In other embodiments, for example, the reinforcement 24 may be free of the panel 28. In other embodiments, the panel 28 may still be used, but, depending on the desired end use of the reinforcement 24, the fenestration 30 may not be included. In some embodiments, there may be more than one fenestration 30 may be included.

The pouches 17a, 17b are attached to the drape 10 at its corners by four generally rectangular portions 32a, 32b, 32c, 32d. In some embodiments, the four generally rectangular portions may be from about 28 inches to about 34 inches deep and from about 50 inches to about 61 inches long. In some embodiments, the generally rectangular portion 32a, 32b, 32c, 32d are about 31 inches deep and about 56 inches wide. These dimensions may vary. The dimensions may vary depending on drape design or the drape's intended use. The four generally rectangular portions 32a, 32b, 32c, 32d may also be made of KRATON™, or any other stretchable, elastic, elastomeric material, or any other material which allows the pouches 17a, 17b to expand during surgery. Because the pouches 17a, 17b are able to expand (due to the pouch's elasticity and the elasticity of the four generally rectangular portions 32a, 32b, 32c, 32d), it is better able to support the weight of whatever is in the pouches 17a, 17b, e.g., a limb, fluid, and/or surgical instruments. Also, because the portions 32a, 32b, 32c, 32d stretch, there is less likelihood of the pouches tearing away from the drape 10 during the surgery. The present embodiment has been described with four generally rectangular elastomeric portions, however, any other number of elastomeric portions may be used. The elastomeric portions 32*a*, 32*b*, 32*c*, 32*d* may be formed of any suitable shape, such as square-shaped, circular-shaped, etc. In other embodiments, the portions may be utilized in regions other than the four corners. Also, in some embodiments, the portions need not be elastomeric.

The pouches 17*a*, 17*b* may also include a at least one tube holder or line holder 35 to place one or more surgical tubes or lines (not shown), such as lines for pneumatic, electric, and battery powered surgical instruments. The tube holder(s) 35 help keep the surgical lines clear of the fenestration 30. The tube holder(s) 35 may also be used to segment, close, or separate, the pouches 17*a*, 17*b* into portions. In the embodiment illustrated in FIG. 1, tabs form tube holder(s) 35 are offset in order to make lifting them easy for the user. In one embodiment, the tabs of the tube holders 35 are made of hook and loop fasteners, such as VELCRO®, however, other fastening means may be used such as buttons, snaps, adhesives, etc. In other embodiments, the tube holders 35 could be attached to the other side of the drape 10 (and not be attached to the pouches 17*a*, 17*b*).

Turning now to FIG. 2, the drape 10 is shown from the patient's (i.e., proximal) side. In this embodiment, the drape 10 includes a second fenestration 36 to receive the patient's leg (or other body part) during surgery. In some embodiments, there may be more than one second fenestration 36 to accept a second limb or a tool that needs to be inserted through the drape 10. The second fenestration 36 is located in a second panel 38. The second panel 38 is attached to the drape 10 via an adhesive glue or surgical tape. Other types of fasteners may also be used such as other types of tape, snaps, buttons, hook and loop fastener, such as VELCRO®, and/or other suitable fasteners. The dimensions and shapes of the second fenestration 36 are generally the same as the first fenestration 30, although the dimensions and shapes of the second fenestration 36 may vary from those of the first fenestration 30. The dimensions and shapes of the second fenestration 36 may be varied depending on the size of the size of the first fenestration 30, the size of the limb to be held, the size of the drape, the position of the drape 10 on the body (e.g., where on the body the drape 10 will be covering), etc. . . . In some embodiments, the second fenestration 36 may be elastomeric, while in other embodiments, the second fenestration 36 may not be elastomeric.

In one embodiment, the second panel 38 is elastomeric, which allows the second fenestration 36 to stretch so as to conform to the patient's leg (or other body part, such as an arm). The second panel 38 may also be made of KRATON™, or any other elastomeric, elastic, and/or stretchable material. The second panel 38 has a width from about 7 inches to about 15 inches and a length of about 7 inches to about 15 inches. The dimensions of the second panel 38 may vary. The dimensions of the second panel 38 may vary depending on the size of the first panel 28, the size of the drape, the type of operation, etc. . . . As with the first panel 28, although the second panel 38 is shown as being generally square, any shape may be used. In some embodiments, the proximal side of the drape 10 may be free of a second fenestration and/or a second panel 38.

In the embodiment illustrated in FIG. 2, there are anti-slip patient positioners 40 adjacent to the second panel 38. The anti-slip patient positioners 40 help keep the drape 10 in place during the surgery. In some other drapes, the drape may slip during the procedure, causing the surgical site to become contaminated or obstructed, or otherwise interrupt the surgical procedure. The anti-slip patient positioners 40, however, provide greater friction between the drape 10 and the patient's body or other underlying materials such as sheets, impervious drapes, or towels, reducing the likelihood of slippage. In one embodiment, the anti-slip patient positioners 40 are two foam strips, located just above and below the second panel 38, about 10 inches to about 15 inches from the second panel 38. In some embodiments, the anti-slip patient positioners 40 are on opposite sides of the fenestration 30. In one embodiment, the anti-slip patient positioners are about 12 inches from the second panel 38. The distance between the anti-slip patient positioners 40 and the second panel 38 may vary from these values. The distance between the anti-slip positioners 40 and the second panel 38 and/or the second fenestration 36 may vary depending on the size of the drape, the intended use of the drape, the intended interaction with the patient, etc . . . There may be any number of anti-slip patient positioners 40 located anywhere on the surgical drape 10. Also, the anti-slip patient positioners 40 may be manufactured of any material that provides friction.

The above embodiments all disclose a drape that includes at least one fenestration. However, the drape(se) described herein may alternatively or additionally, the drape may include splits and/or cut-outs that are formed around the limbs.

Although the above embodiments are described in relation to drape(s) to be used during hip surgery, it should be understood that the drape(s) and pouches can be used in any type of surgery, especially those in which a limb needs to be supported by the pouches during the surgery.

Furthermore, although the description above describes a surgical drape, a method of manufacturing the drape 10 is also contemplated. In one embodiment, the method includes attaching the pouches of panels 16, 18 to the distal side of the drape 10, such that the elastomeric portions 32*a*, 32*b*, 32*c*, 32*d* allow the pouch to stretch away from the sheet.

According to another method of making the surgical drape 10, the fastener 20 is attached to a portion of proximal side of the drape 10 and the anti-slip patient positioner 40 is attached to the proximal side of the drape 10.

According to an alternative embodiment A, a surgical drape comprises a sheet having a distal side and a proximal side relative to a surgical patient; and a surgical pouch connected to the distal side of the sheet, the surgical pouch including at least two elastomeric portions, the at least two elastomeric portions allowing the pouch to stretch away from the sheet.

According to an alternative embodiment B, the drape of alternative embodiment A further comprises a tube holder for holding a surgical tube or surgical line.

According to an alternative embodiment C, the drape of alternative embodiment A wherein the drape includes first and second plastic panels around a surgical site.

According to an alternative embodiment D, the drape of alternative embodiment A wherein the drape includes an elastomeric panel having a fenestration for receiving a limb.

According to an alternative embodiment E, the drape of alternative embodiment A wherein the pouch includes four elastomeric portions, one of the four elastomeric portions located at each of the four corners of the pouch.

According to an alternative embodiment F, the drape of alternative embodiment A wherein the pouch is a fluid impervious clear plastic.

According to an alternative embodiment G, the drape of alternative embodiment A wherein the proximal side of the sheet includes a fenestration for receiving a limb.

According to an alternative embodiment H, the drape of alternative embodiment A wherein the proximal side of the sheet includes an anti-slip patient positioner adapted to keep the drape from slipping.

According to an alternative embodiment I, a method of making a surgical drape comprises providing a sheet having a distal side and a proximal side relative to a surgical patient, providing a pouch including a plurality of elastomeric portions, and attaching the pouch to the sheet, wherein the plurality of elastomeric portions allow the pouch to stretch away from the sheet.

According to an alternative embodiment J, the method of alternative embodiment I further comprising attaching a tube holder to the sheet, the tube holder for holding at least one surgical tube.

According to an alternative embodiment K, the method of alternative embodiment I wherein the drape includes an elastomeric panel having a fenestration for receiving a limb.

According to an alternative embodiment L, the method of alternative embodiment I wherein the plurality of elastomeric portions includes four elastomeric portions, one of the four elastomeric portions located at each of the four corners of the pouch.

According to an alternative embodiment M, the method of alternative embodiment I wherein the pouch is a fluid impervious clear plastic.

According to an alternative embodiment N, the method of alternative embodiment I wherein the proximal side of the sheet includes a fenestration for receiving a limb.

According to an alternative embodiment O, the method of alternative embodiment I further comprising attaching an anti-slip patient positioner onto the proximal side of the drape.

According to an alternative embodiment P, a surgical drape comprises a distal side and a proximal side relative to a surgical patient, the proximal side of the drape including a fastener for attaching the drape to a surface and at least one anti-slip patient positioner for holding the drape in place on the patient.

According to an alternative embodiment Q, the surgical drape of alternative embodiment P wherein the drape is a T-shaped drape for use in hip surgery.

According to an alternative embodiment R, the surgical drape of alternative embodiment P wherein the proximal side includes a fenestration adapted to receive a limb and at least two anti-slip patient positioners on opposite sides of the fenestration.

According to an alternative embodiment S, the surgical drape of alternative embodiment R wherein the at least two anti-slip patient positioners are foam strips.

According to an alternative embodiment T, the surgical drape of alternative embodiment P wherein the proximal side further includes a fenestration adapted to receive a limb, the fenestration being within an elastomeric panel adapted to stretch around the limb of the patient.

According to an alternative embodiment U, the surgical drape of alternative embodiment P further comprising a pouch attached to the distal side of the drape, the pouch including a plurality of elastomeric portions allowing the pouch to stretch away from the distal side of the drape.

According to an alternative embodiment V, a method of making a surgical drape comprises providing a surgical drape having a distal side and a proximal side relative to a surgical patient's body, attaching a fastener to at least a portion of proximal side of the drape, the fastener for attaching the drape to a surface, and attaching an anti-slip patient positioner to the proximal side of the drape, the anti-slip patient positioner for contacting the surgical patient during surgery.

According to an alternative embodiment W, the method of alternative embodiment V further comprising attaching a pouch the pouch including a plurality of elastomeric portions allowing the pouch to stretch away from the distal side of the drape.

According to an alternative embodiment X, the method of alternative embodiment V further comprising attaching a tube holder to the drape for holding at least one surgical tube during the surgery.

According to an alternative embodiment Y, the method of alternative embodiment V wherein the anti-slip patient positioner is at least two foam strips.

According to an alternative embodiment Z, a surgical drape comprises a sheet having a distal side and a proximal side relative to a surgical patient; and a surgical pouch connected to the distal side of the sheet, the surgical pouch including at least two elastomeric portions, the at least two elastomeric portions allowing the pouch to stretch away from the sheet.

According to yet an alternative embodiment AA, the drape of alternative embodiment Z, wherein the drape includes first and second panels around a surgical site.

According to yet another embodiment AB, the method of claim V, further comprising attaching a pouch to the distal side of the drape, the pouch including a plurality of elastomeric portions allowing the pouch to stretch away from the distal side of the drape.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A surgical drape comprising:
   a sheet having a distal side and a proximal side relative to a surgical patient, the proximal side being adjacent to the patient;
   an expandable surgical pouch connected to the distal side of the sheet, the expandable surgical pouch being made at least in part from an elastic material for allowing the expandable surgical pouch to stretch during surgery; and
   at least two separate and distinct elastomeric portions attached to the distal side of the sheet, the elastomeric portions connecting the expandable surgical pouch to the distal side of the sheet such that it allows the expandable surgical pouch to stretch away from the sheet, the elastomeric portions being the sole attachment points between the pouch and the sheet, each of the elastomeric portions having an overlapping area and a nonoverlapping area, the pouch being attached to the sheet via the overlapping area of the elastomeric portions, the nonoverlapping area being free to move relative to the sheet when the expandable surgical pouch is stretched away from the sheet to minimize likelihood of tearing of the expandable surgical pouch.

2. The drape of claim 1, further comprising a tube holder for holding a surgical tube.

3. The drape of claim 1 wherein the drape includes first and second panels around a surgical site.

4. The drape of claim 1 wherein the drape includes an elastomeric panel having a fenestration for receiving a limb.

5. The drape of claim 1 wherein the pouch includes four corners, the at least two elastomeric portions being four elastomeric portions, each of the four elastomeric portions being located at one of the four corners of the pouch.

6. The drape of claim 1 wherein the pouch is a fluid impervious clear plastic.

7. The drape of claim 1 wherein the proximal side of the sheet includes a fenestration for receiving a limb.

8. The drape of claim 1 wherein the proximal side of the sheet includes an anti-slip patient positioner adapted to keep the drape from slipping.

9. A method of making a surgical drape comprising:
   providing a sheet having a distal side and a proximal side relative to a surgical patient, the proximal side being adjacent to the patient;
   providing an expandable pouch, the expandable pouch being made at least in part from an elastic material for allowing the expandable surgical pouch to stretch during surgery; and
   attaching the pouch to the distal side of the sheet via at least two separate and distinct elastomeric portions, wherein the plurality of elastomeric portions allow the pouch to stretch away from the sheet, the elastomeric portions being the sole attachment points between the pouch and the sheet, each of the elastomeric portions having an overlapping area and a nonoverlapping area, the pouch being attached to the sheet via the overlapping area of the elastomeric portions, the nonoverlapping area being free to move relative to the sheet when the expandable surgical pouch is stretched away from the sheet to minimize likelihood of tearing of the expandable surgical pouch.

10. The method of claim 9, further comprising attaching a tube holder to the sheet, the tube holder for holding at least one surgical tube.

11. The method of claim 9 wherein the drape includes an elastomeric panel having a fenestration for receiving a limb.

12. The method of claim 9 wherein the plurality of elastomeric portions includes four elastomeric portions and the pouch includes four corners, each of the four elastomeric portions being located at one of the four corners of the pouch.

13. The method of claim 9 wherein the pouch is a fluid impervious clear plastic.

14. The method of claim 9 wherein the proximal side of the sheet includes a fenestration for receiving a limb.

15. The method of claim 9, further comprising attaching an anti-slip patient positioner onto the proximal side of the drape.

16. A surgical drape comprising a distal side and a proximal side relative to a surgical patient, the proximal side of the drape including a fastener for attaching the drape to a surface and at least one anti-slip patient positioner for holding the drape in place on the patient, the anti-slip patient positioner providing greater friction than the drape, the drape further including a plurality of distinct elastomeric portions as the sole attachment points for a surgical pouch, the plurality of distinct elastomeric portions including at least two separate and distinct elastomeric portions, the surgical pouch being made at least in part from an elastic material for allowing the surgical pouch to stretch during surgery, the elastomeric portions connecting the surgical pouch to the distal side of the surgical drape such that it allows the surgical pouch to stretch away from the surgical drape, each of the elastomeric portions having an overlapping area and a nonoverlapping area, the surgical pouch being attached to the surgical drape via the overlapping area of the elastomeric portions, the nonoverlapping area being free to move relative to the surgical drape when the expandable surgical pouch is stretched away from the surgical drape to minimize likelihood of tearing of the surgical pouch.

17. The surgical drape of claim 16 wherein the drape is a T-shaped drape for use in hip surgery.

18. The surgical drape of claim 16 wherein the proximal side includes a fenestration adapted to receive a limb and at least two anti-slip patient positioners on opposite sides of the fenestration.

19. The surgical drape of claim 18 wherein the at least two anti-slip patient positioners are foam strips.

20. The surgical drape of claim 16 wherein the proximal side further includes a fenestration adapted to receive a limb, the fenestration being within an elastomeric panel adapted to stretch around the limb of the patient.

21. The surgical drape of claim 16, wherein the surgical pouch is attached to the distal side of the drape such that the pouch can stretch away from the distal side of the drape.

22. A method of making a surgical drape comprising:
   providing a surgical drape having a distal side and a proximal side relative to a surgical patient's body;
   attaching a fastener to at least a portion of the proximal side of the drape, the fastener for attaching the drape to a surface;
   attaching an anti-slip patient positioner to the proximal side of the drape, the anti-slip patient positioner for contacting the surgical patient during surgery and providing greater friction than the drape; and
   attaching a surgical pouch to the drape solely via at least two separate and distinct elastomeric portions, each of the elastomeric portions having an overlapping area and a nonoverlapping area, the surgical pouch being attached to the surgical drape via the overlapping area of each of the elastomeric portions, the nonoverlapping area of each of the elastomeric portions being free to move relative to the surgical drape when the surgical pouch is stretched away from the surgical drape to minimize likelihood of tearing of the surgical pouch, the surgical pouch being made at least in part from an elastic material for allowing the surgical pouch to stretch during surgery.

23. The method of claim 22, further comprising attaching the pouch to the distal side of the drape such that the pouch can stretch away from the distal side of the drape.

24. The method of claim 22 further comprising attaching a tube holder to the drape for holding at least one surgical tube during the surgery.

25. The method of claim 22 wherein the anti-slip patient positioner is at least two foam strips.

* * * * *